(12) United States Patent
Liberatore et al.

(10) Patent No.: US 7,594,429 B2
(45) Date of Patent: Sep. 29, 2009

(54) SYSTEM AND METHOD FOR IMPROVED OPTICAL MEASUREMENTS DURING RHEOMETRIC MEASUREMENTS

(75) Inventors: Matthew Liberatore, Arvada, CO (US); Norman Wagner, Newark, DE (US); Nigel Doe, Horsham (GB)

(73) Assignees: Waters Investments Limited, New Castle, DE (US); University of Delaware, Newark, DE (US)

( * ) Notice: Subject to any disclaimer, the term of this patent is extended or adjusted under 35 U.S.C. 154(b) by 280 days.

(21) Appl. No.: 11/603,087

(22) Filed: Nov. 22, 2006

(65) Prior Publication Data
US 2007/0193343 A1      Aug. 23, 2007

Related U.S. Application Data

(60) Provisional application No. 60/738,976, filed on Nov. 23, 2005, provisional application No. 60/741,868, filed on Dec. 5, 2005.

(51) Int. Cl.
*G01N 11/10* (2006.01)
(52) U.S. Cl. .................................. 73/54.23
(58) Field of Classification Search ............ 73/54.23, 73/54.27, 54.29, 54.33, 54.39; 356/72
See application file for complete search history.

(56) References Cited

U.S. PATENT DOCUMENTS

| 4,602,501 A * | 7/1986 | Hirata ................. 73/54.23 |
|---|---|---|
| 4,763,512 A * | 8/1988 | Taylor ................. 73/54.27 |
| 5,040,410 A * | 8/1991 | Chu et al. .............. 73/54.01 |
| 5,151,748 A * | 9/1992 | Bur et al. .............. 356/32 |
| 5,327,778 A * | 7/1994 | Park .................. 73/54.21 |
| 6,484,567 B1 * | 11/2002 | Hajduk et al. ........... 73/54.37 |
| 2002/0116987 A1 * | 8/2002 | Braithwaite et al. ...... 73/54.01 |
| 2007/0266776 A1 * | 11/2007 | Liberatore et al. ....... 73/54.23 |
| 2008/0047328 A1 * | 2/2008 | Wang .................. 73/54.39 |

OTHER PUBLICATIONS

Fuller, Gerald (1995). *Optical Rheometry of Complex Fluids*. New York, NY: Oxford University Press. pp. 52-76, 149-180, 181-192.

(Continued)

*Primary Examiner*—John Fitzgerald
(74) *Attorney, Agent, or Firm*—Aslan Baghdadi; Paul, Hastings, Janofsky & Walker LLP (57) ABSTRACT

A rheometric system includes an optical encoder coupled to a rotating shaft and configured to detect a rotational position of the shaft with respect to a reference. The rotational information is forwarded to a program or memory. An optical rotation plate is mechanically fastenable to the rotating shaft. A laser is provided to probe optical properties of a fluid sample proximate to the optical rotation plate. The system includes a detector system for measuring laser light scattered or transmitted through the sample chamber. The detector system is coupled to a memory that stores optical data collected after light impinges on the optical plate. Experimental fluid sample optical data and background optical data are each stored as a data structure that creates a point by point map of rotational position of the sample plate with the optical data collected thereat. A program or routine is provided that can correct point by point along the optical rotation plate the experimental sample optical data using the background optical data.

22 Claims, 7 Drawing Sheets

OTHER PUBLICATIONS

Liberatore, M., & McHugh, A. (2005). Dynamics of shear-induced structure formation in high molecular weight aqueous solutions. *Journal of Non-Newtonian Fluid Mechanics*. 132, 45-52.

van Egmond, J., Werner, D., & Fuller, G. (1992). Time-dependent small-angle light scattering of shear-induced concentration fluctuations in polymer solutions. *J. Chem. Phys*. 96, 7742-7757.

* cited by examiner

SYSTEM AND METHOD FOR IMPROVED OPTICAL MEASUREMENTS DURING RHEOMETRIC MEASUREMENTS

This application claims priority to U.S. Provisional Patent Application No. 60/738,976, filed Nov. 23, 2005, and to U.S. Provisional Patent Application No. 60/741,868, filed Dec. 5, 2005, both of which are incorporated by reference herein in their entirety.

BACKGROUND

1. Field of the Invention

The present invention relates generally to materials testing and in particular to improvements in optical rheometric testing.

2. Background of the Invention

Figures 1A, 1B, 1C:
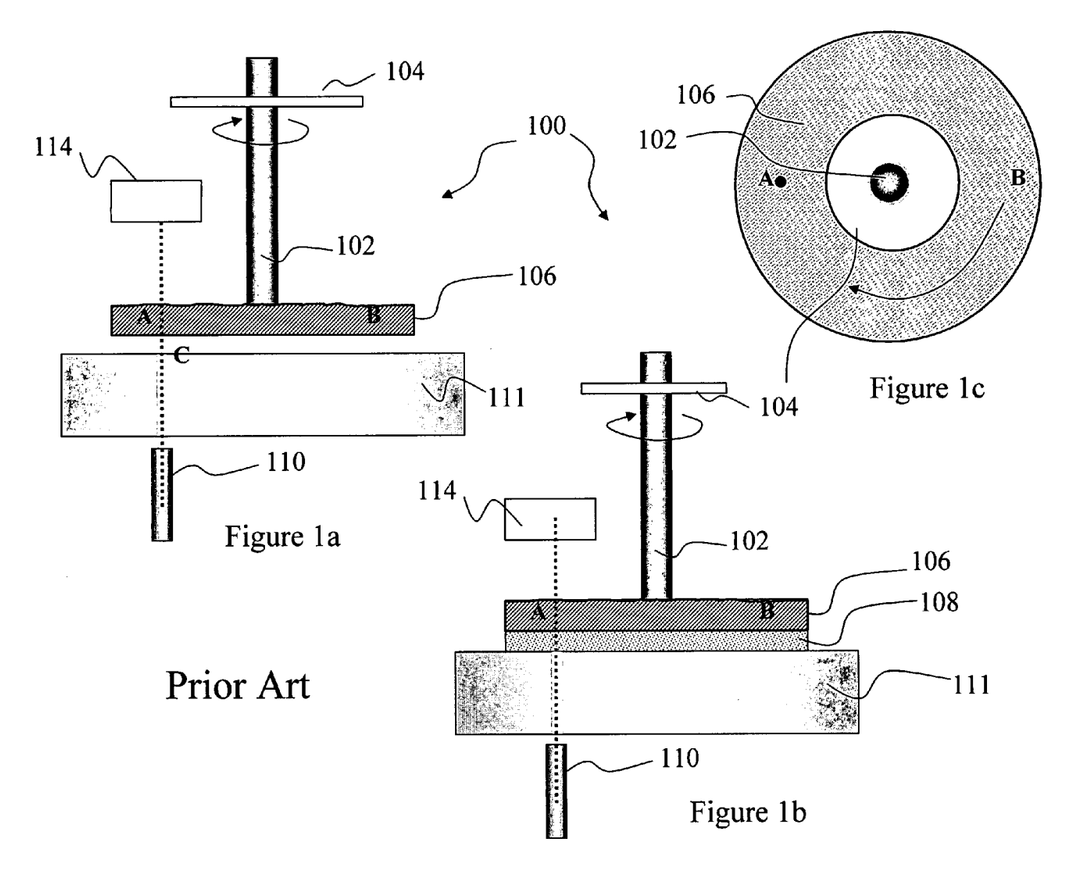

Rheometers are widely used to measure viscoelastic properties of fluid materials such as liquids, polymers, and granular solids. As used herein, the term "rheometer" encompasses instruments also referred to as viscometers or viscosometers. A common type of rheometer is a rotational rheometer that typically involves a central shaft attached to a rotating element placed in a sample container. Two distinct types of rotational rheometers are commonly used: a separate motor and transducer (SMT) rheometer and a combined motor and transducer (CMT) rheometer. FIGS. 1a-c illustrate a CMT rheometer 100 having a known arrangement in which the drive system for shaft 102 and measuring transducer 104 are located along a common axis. When a rotation or oscillation is introduced into shaft 102, quartz plate 106 attached thereto rotates in a concentric manner with shaft 102, so that movement or shear can be induced in fluid 108, while lower plate 111 remains fixed. Displacement transducer 104 can be used to determine shear stress introduced in the fluid when a rotational movement is introduced into plate 106. Accordingly, viscoelastic properties of fluid 108 can be studied.

For many applications, in addition to studying viscoelastic response, it is desirable to record fluid optical properties and changes in optical properties in-situ in a rheometer. For example, using a light source, such as stationary laser 110, optical properties can be monitored together with viscoleastic response of fluid 108 when plate 106 is rotated. Sample optical properties such as dichroism, birefringence, and small-angle light scattering can typically be measured using the arrangement of system 100 or similar arrangements. When laser light passes through rotating plate 106 and fluid 108, the optical signal, or change in optical signal can be used to determine certain fluid optical properties such as those listed above. For example, taking into account the optical properties of plate 106, the dichroism or birefringence of fluid 108 can be determined.

Known rheometer systems that include such capability to determine fluid optical properties could in principle be used to study such fluid phenomena such as stress induced birefringence, liquid crystalline transitions, order-disorder transitions, in-situ study of curing reactions, and the like. For example, measured changes in dichroism attributable to fluid 108 can be related to such phenomena as phase separation or phase change in the fluid. However, because of unwanted background interference with an optical signal generated by rheometer components, in-situ measurement of optical properties of a sample is often compromised, as discussed below with further reference to FIGS. 1b and 1c.

For example, to account for the effect on signal attenuation due to optical plate 106, a background optical measurement of optical plate 106 could be performed in the absence of an experimental sample. Thus, optical plate 106 can be placed into measurement position and exposed to laser 110 so that laser light passes through plate 111 at point C and plate 106 at point A. This provides a "background" optical signal due to attenuation of the laser by the optical plate 106, which can be recorded by detector 114. Referring now to FIG. 1c, an "experimental" optical measurement can subsequently be recorded at detector 114 with liquid sample 108 present, and the background subtracted from the experimental measurement to provide a more accurate estimate of the liquid sample optical properties. However, during collection of a background measurement, the point A used for background measurement may not be representative of optical plate 106, as described further below.

In the parallel plate rheometer geometry illustrated in FIG. 1a, during an actual rheometric experiment, plate 106 is subject to rotation as shown. Thus, different portions of plate 106 are presented to the laser light of the optical probe as the light passes through the plate. Because plate 106 typically exhibits some degree of non-uniformity, as plate 106 rotates, the optical properties of portions of plate 106 that intercept laser light from laser 110 also vary during rotation. This is because the plate may have surface defects, non-uniform thickness, and other defects that vary according to position on the plate. For example, as plate 106 rotates, moving points A and B on optical plate 106 that are exposed to laser 110 at fixed point C, may have different optical properties. In general, the attenuation of laser light passing through plate 106 at point C can vary as plate 106 rotates, causing variation in the optical signal measured after light from laser 110 passes through fluid 108. Thus, the attenuation of laser 110 during a background measurement taken, for example, at point A on optical plate 106, or at any specific point along optical plate 106 between points A and B, might be much different than the attenuation of light on optical plate 106 during measurement of an actual fluid sample, when the laser light beam may be intercepted by many portions of the optical plate 106. The variation in background attenuation of a transmitted signal due to optical plate non-uniformity may overwhelm or substantially affect dichroism or birefringence effects within fluid 108 during a rheometric measurement, by making it difficult to account for the background optical plate contribution to the signal, and therefore making it hard to accurately determine optical properties or changes in optical properties solely attributable to fluid 108.

BRIEF SUMMARY OF THE INVENTION

In one embodiment of the present invention, a rheometric system having improved optical measurement capabilities includes an optical encoder coupled to a rotating shaft. The encoder is configured to detect a rotational position of the shaft with respect to a reference position. Preferably, the encoder is configured to provide rotational position (also termed "angular position") information over an entire rotation range of the shaft. The system forwards rotational information to a memory so that the rotational information can be correlated to other concurrent measurements, such as optical measurements. The system also includes an optical rotation plate mechanically fastenable to the rotating shaft and configured to rotate within a fluid. A laser is provided to probe optical properties of a sample placed in a sample chamber that encloses the optical rotation plate. The system further includes a detector for measuring laser light scattered or transmitted through the sample chamber. The detector is coupled to a memory that stores optical data collected after the laser light impinges on an experimental fluid sample in the sample chamber. As used herein; the terms "experimental fluid sample," "fluid sample" or "experimental sample" refer to a fluid to be tested by one or more measurements, so that property measurements of the fluid sample can be studied, in contrast to other fluids that may or may not be used to perform calibrations, background measurements, or other functions, but are themselves not the subject of the experiment.

In one example of the invention, experimental fluid sample optical data is collected by passing the laser light through the experimental fluid sample during rotation of the optical plate, such that point by point measurements corresponding to different points along a circumference of the plate are collected, and subsequently stored in the memory. Preferably, the experimental fluid sample optical data is stored as a data structure that creates a point by point mapping of a rotational position of the sample plate with the optical data collected thereat. Background sample optical data collected when no experimental fluid sample is present can likewise be measured point by point as a function of rotational position of the optical rotation plate, and stored in a data structure. A program or routine is provided that can compare point by point along the optical rotation plate the background optical data with the experimental sample optical data. Comparison can be performed, for example, by subtracting each background optical measurement from its corresponding experimental sample optical measurement at any given set of common points on the optical plate. In this manner, much more sensitive and accurate optical data can be collected from the experimental fluid sample.

In another embodiment of the present invention, a method for improved measurement of optical properties of a fluid in a rheometer includes the steps of: providing a light beam towards a rotatable optical plate; recording background optical measurements of light from the light beam transmitted through the rotatable optical plate when the optical plate is arranged at a set of angular positions; mapping the set of angular positions to the respective background optical measurements; providing a fluid sample in intimate contact with the rotatable optical plate; recording sample optical measurements of light from the light beam transmitted through the rotatable optical plate (also simply termed "optical plate") and fluid sample when the optical plate is arranged at the set of predetermined angular positions; mapping the set of angular positions to the respective sample optical measurements; mapping the background optical measurements to the sample optical measurements based on the set of angular positions; and manipulating respective sample optical measurements and background optical measurements to produce a set of background corrected optical fluid sample data.

BRIEF DESCRIPTION OF THE DRAWINGS

FIGS. 1a and 1b, respectively depict a side view of a known rheometer with and without fluid sample present.

FIG. 1c depicts a plan view of the rheometer of FIG. 1a.

DETAILED DESCRIPTION OF THE INVENTION

Figures 2A, 2B, 2C:
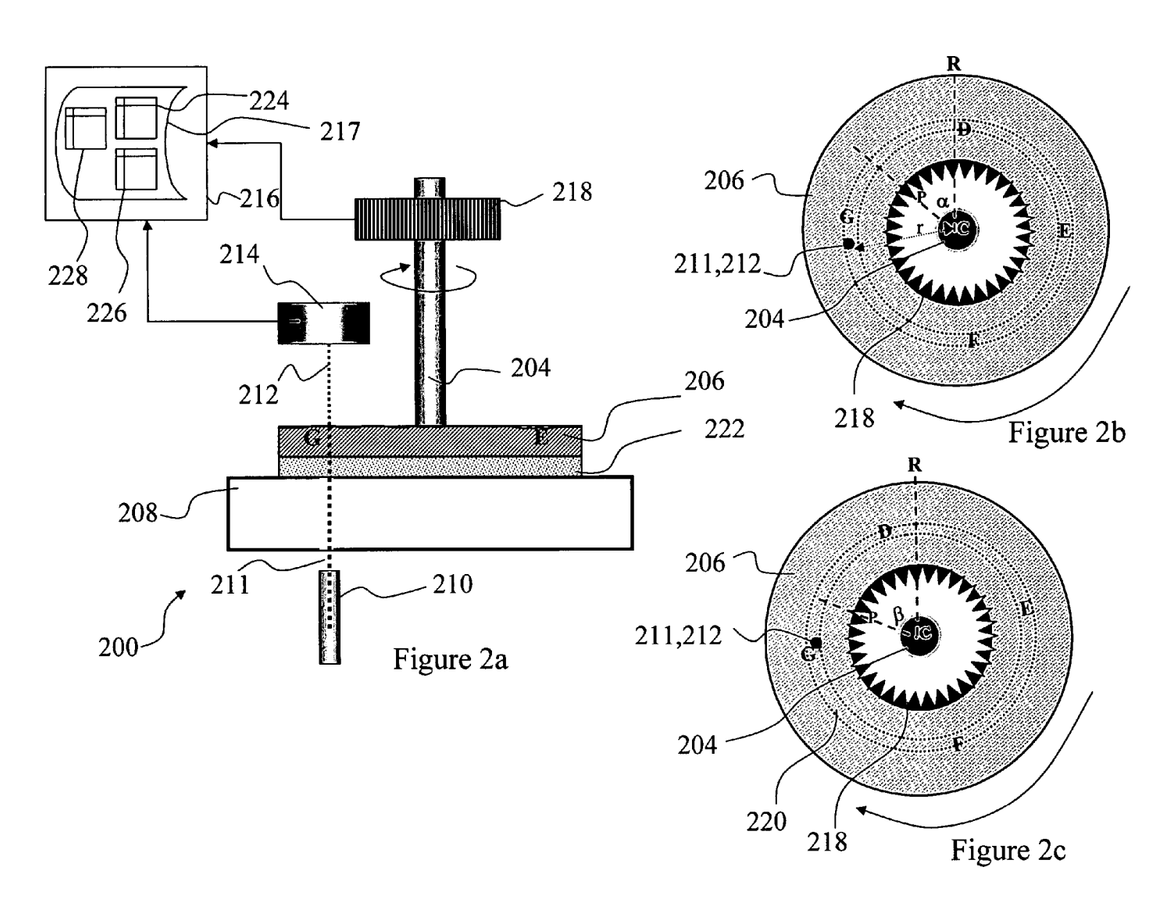
FIGS. 2a and 2b-c depict a side view and plan views, respectively, of a system that provides improved optical measurement capability during rheometric measurement, according to an embodiment of the present invention.

FIG. 2a depicts features of a system 200 that provides improved optical measurement capability during rheometric measurement, according to an embodiment of the present invention. System 200 provides the capability of performing rheometric measurements of fluid samples 209 placed between plates 206 and 208. System 200 also includes the capability of making optical measurements of fluid samples using laser 210 and detector 214. System 200 and other additional embodiments of this invention will be also referred to as a "rheometer" although it will be understood that the system provides for optical measurements in addition to "rheometric" measurements, such as shear stress and strain.

Rotatable shaft 204 is driven by a motor (not shown) and can rotate or oscillate around an axis parallel to the long direction of the shaft. Rotatable optical plate 206 is mechanically fastenable to and removable from shaft 204. When fastened to shaft 204, optical plate 206 rotates in unison with shaft 204. Properties of a fluid sample placed in system 200 can be measured in a number of ways. For example, rotation of optical plate 206 above module 208 can be used to introduce a shear force within a fluid sample (see FIG. 2c). A torque can thus be applied to plate 206 and a response velocity measured using, for example, an accelerometer (not shown), from which the viscoelastic properties of the sample are extracted.

Laser 210 can be used as a probe to facilitate measurement of optical properties of a fluid sample. For example, while a rotation or oscillation is introduced into optical plate 206, laser 210 can emit incident beam 211 which can pass through fluid sample 209 and optical plate 206, forming transmitted beam 212 that is received at detector 214. Preferably, optical plate 206 is a relatively transparent material, so that the intensity of transmitted beam 212 can be readily measured. An incoming transmitted light signal from transmitted beam 212 can be formed in detector 214 and sent to processor 216 for storage in a memory 217. Thus, optical properties of a fluid sample can be measured and stored concurrently with measurement of viscoelastic properties. As described further below, in accordance with one embodiment of the present invention, system 200 provides the ability to correct a series of experimental optical measurements performed with a fluid sample present, by mapping the experimental measurements to a respective series of "background" optical measurements performed in the absence of a fluid sample.

System 200 further includes post-laser module 208. Laser 210 and post-laser module 208 comprise a lead optics module (not shown). In one embodiment of the present invention, post laser module 208 includes, in consecutive order between laser 210 and rotating optical plate 206, a polarizer, photoelastic modulator (PEM), quarter wave plate and heating plate that substantially passes an incident beam (all not shown). Post-laser module 208 thus provides an arrangement to polarize beam 211 emitted from laser 210 and conduct birefringence experiments by manipulating beam 211 using the polarizer, PEM and quarter wave plate, and by measuring transmitted beam 212 after it passes through an analyzer (not shown). For example, a photoelastic modulator contained in module 208 can be used to receive a polarized beam passing out of the polarizer and to pass a modulated beam that contains one component of the polarized beam that is retarded with respect to a second component. After interacting with optical plate 206 and fluid sample 209, polarized components of beam 212 can be passed through an analyzer and exit as an analyzed beam recorded by detector 214. The analyzed beam can provide information useful in determining birefringence, dichroism and other related fluid sample properties that admit of study using polarized beams.

System 200 includes position transducer 218 that is capable of registering a position of rotating shaft 204 with respect to a reference point (not shown). Preferably, position transducer 218 is a rotation optical encoder attached to shaft 204 for registering an angular position of a point on shaft 204 with respect to a reference point. FIGS. 2b and 2c illustrate top views of portions of system 200 at two different rotational positions of optical plate 206 with respect to beam 210. As viewed from the perspective of FIG. 2b, the term "angular position" refers to an angle formed by a point on a rotating object, such as optical shaft 204 or optical plate 206, with respect to a fixed point. As depicted in FIGS. 2b-c, points D-G rotate in unison with point P on position transducer 218. Thus, in FIG. 2b, point P forms an angular position □, with respect to a reference point R. In FIG. 2c, when the angular position of P with respect to R is β, point G on optical plate 206 intersects laser beam 211, 212. Thus, angular position β, which can be recorded by transducer 218, corresponds to the position in which the measured light signal at detector 214 is attenuated by point G on optical plate 206.

In the example shown in FIG. 2c, the radial distance of points D-G from point C corresponds to the distance r of transmitted beam 212 from point C. Thus, points D-G all rotate through the position of beam 212 as optical plate 206 performs a revolution. For example, when point G intercepts the laser beam, transmitted beam 212 is the result of the interaction of incident beam 211 and the region of optical plate 206 represented by point G. In addition to the effects of light attenuation and scattering due to the nominal properties of optical plate 106, any irregularities, imperfections, impurities, or other microstructural or macrostructural features in the region of G can also affect the amount and nature of transmitted light beam 212. By registering the angular position of transducer (also termed "encoder") 218 at the time when point G intersects beam 211, the optical signal from beam 212 recorded at the same time can be associated with (mapped to) point G. Similarly, the optical properties of plate 206 at points D-F, as well as any points lying within annular region 220 (concentric with the rotation axis of shaft 204), can be mapped. Annular region 220 corresponds to the region of optical plate 206 that is intersected by beam 211 during rotation of the plate.

In one embodiment of the present invention, a set of background optical measurements is taken by detector 214 as optical plate 206 is rotated through a rotation arc. The set of optical measurements is mapped to a corresponding set of plate positions, such that each optical measurement is associated with a distinct plate position on optical plate 206. Since optical plate 206 rotates in unison with encoder 218, the set of distinct plate positions can be denoted, for example, by reference to a set of corresponding encoder positions, as described above. In one embodiment, the set of background optical measurements is taken at equally spaced angular intervals over an entire 360 degree arc of optical plate 206. The background optical measurements can be taken in an empty rheometer without any fluid, or in the presence of a fluid medium that assists in optical measurement, for example, an index-matching fluid described below.

Subsequently, a set of experimental optical measurements of transmitted beam 212 is recorded by detector 214 when optical plate 206 is rotated through a set of specified plate positions in the presence of fluid sample 209 whose properties are to be studied. In one embodiment of the present invention, the experimental optical measurements can be performed simultaneous with viscloelastic measurements. Preferably, the specified plate positions corresponding to the set of experimental optical measurements have a one to one correspondence with the set of plate positions used for background optical measurement. In other words, for each plate position in which a background optical measurement is recorded, a corresponding experimental sample measurement is also recorded. Accordingly, a background optical measurement for each recorded position of optical plate 206 can be mapped to a corresponding experimental fluid sample optical measurement taken at the same plate position. In this manner, the background optical data for any given recorded point on plate 206 can be used to correct the experimental fluid sample optical data at that point. For example, processor 216 could perform a correction of experimental fluid sample data using the background data and a program or routine designed to manipulate the experimental data, such as subtracting the background data from the experimental sample data. In this manner, the background contribution caused by even a large variation in optical plate properties over region 220 can be effectively be eliminated from experimental data, as illustrated in the conceptual diagrams of FIG. 3a and 3b.

Figure 3A:
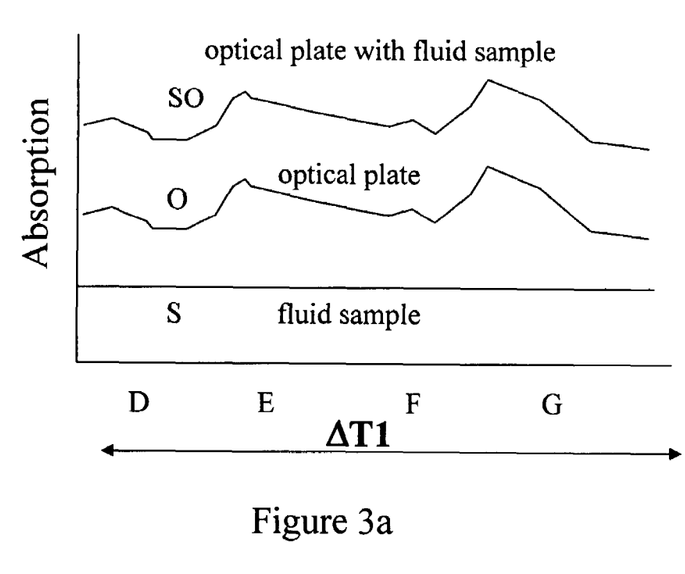
FIGS. 3a and 3b illustrate possible sample curves obtained according to the operation of the system of FIGS. 2a-c.

In FIG. 3a, curve S represents laser light absorption at a time interval ΔT, for an experimental fluid sample placed in a rheometer chamber, shown as a function of plate position (or time) for a rotating optical plate. Referring also to FIG. 2a, the absorption could be derived, for example, from a comparison of the intensity of incident beam 211 and transmitted beam 212 using detector 214. As optical plate 206 rotates, the intensity of transmitted beam 212 can be recorded at a set of predetermined positions, producing a series of absorption values that produce curve SO. Even though light attenuation from fluid sample 222 itself may be relatively spatially uniform (as shown in this example by curve S), curve SO nonetheless may exhibit peaks and valleys due to non-uniform absorption by optical plate 206, as discussed above.

A set of measurements that produce "background" curve O can be taken shortly before or shortly after those for curve SO are obtained. The data for curve O are produced when no experimental fluid sample is present. The peaks and valleys in curve O can be attributed to non-uniformity in laser light absorption as a function of plate position on optical plate 206. Preferably, both curves SO and O are taken at the same set of plate positions. Curve O can be compared to curve SO to extract a curve S that is representative of light absorption of the fluid sample alone. For example, the comparison of curves SO and O can involve a simple subtraction of the latter from the former. In this case, the fluid sample is shown to have uniform absorption as a function of position.

Figure 3B:
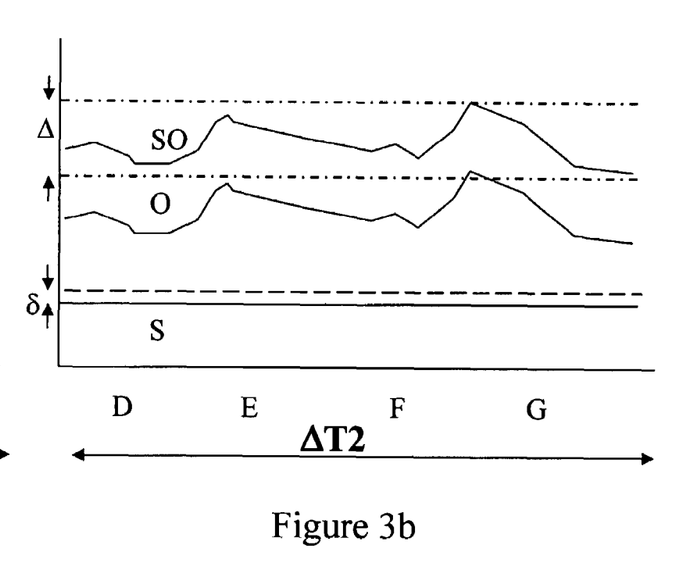

FIG. 3b shows a similar set of curves to those of FIG. 3a taken at a time interval ΔT2. In this case, curve O is assumed to be the same "background" optical plate curve as that of FIG. 3a. In this case, the absorption characterized by curve SO is seen to be somewhat less than that of its counterpart in FIG. 3a. Accordingly, the absorption of the fluid sample curve S is also reduced compared to that in FIG. 3a (also plotted in FIG. 3b as a dashed line). Variations between absorption recorded over interval ΔT1, as opposed to ΔT2 (where the time intervals do not overlap in real time) may be associated with any number of factors whose time dependence causes a change in fluid sample absorption. For example, FIGS. 3a and 3b may correspond to two measurements of a birefringent fluid sample that are taken under two different polarizer conditions. Thus, a comparison of the effect on fluid sample optical properties from changed conditions can be obtained according to the procedures illustrated in FIGS. 3a and 3b.

Notably, although in the example shown in FIG. 3b the difference δ between recalculated fluid sample S absorption at two different time intervals ΔT1, ΔT2 is small in absolute value as compared to the variation Δ of optical absorption across the optical plate, this difference is easily discernible because the S curves at each time interval are relatively flat (non-noisy). The flatness results from the ability to correlate pairs of recorded absorption values where one of each pair is taken before and the other taken after an experimental fluid sample is introduced into a rheometer chamber. Thus, high absorption points from curve O are subtracted from high absorption points from curve SO, low absorption points on curve O are subtracted from low absorption points from curve SO, and so forth.

Although, the above example in FIGS. 3a and 3b was illustrated using a linear subtraction of curve O from SO to obtain fluid sample curve S, it is to be emphasized that embodiments of the present invention are contemplated in which any useful procedure can be used to correlate groups of optical data collected with ("sample") and without ("background") experimental fluid sample present, provided that each group of optical data corresponds to a set measurements that can be point by point mapped to a set of known locations (points) on a rotating optical plate. "Point by point mapping" denotes the associating of each individual measurement of a set of one or more distinct sets of measurements with a specified point on an optical plate from which the measurement was derived. Thus, any procedure used to manipulate background and sample optical data based on point by point mapping so as to account for the effect of the background data will fall within the scope of this invention.

Similarly, the term "point by point" subtraction refers to the subtraction of a first set of data comprising a plurality of optical values from a second set of data comprising a second plurality of optical values, wherein each datum within the first set of data corresponds to the same plate location (point) as that of the datum in the second set of data from which the datum in the first set is subtracted.

Figure 4:
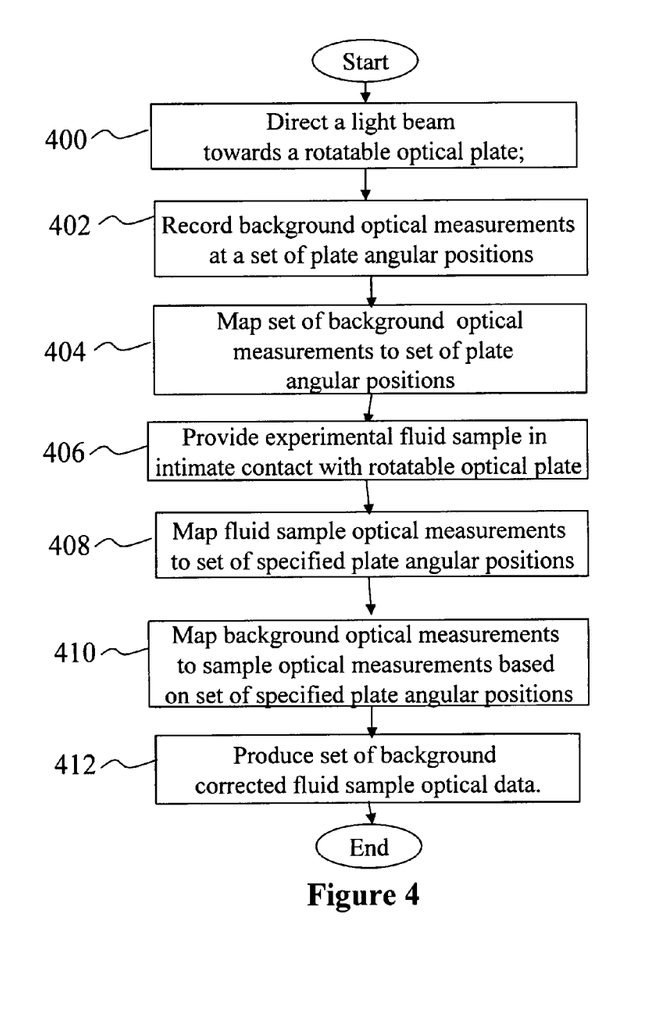
FIG. 4 illustrates exemplary steps involved in a method for improved optical measurements of a sample in a rheometric system, according to another embodiment of the present invention.

FIG. 4 illustrates a method for improved optical measurement of a sample in a rheometric system, according to another embodiment of the present invention.

In step 400, a light beam is directed towards a rotatable optical plate located within the rheometric system. Generally, the rotatable optical plate is configured to impart stress or strain to an experimental fluid sample placed in the rheometric system, either by rotation or oscillation of the plate. Generally, the rotatable optical plate is substantially transparent so that light transmission measurements of a beam passing through the plate and a proximate fluid sample can be easily performed. The light beam may comprise a collimated beam, a laser beam, or other convenient light source. The light beam can be a circularly polarized beam, a linearly polarized beam, or an unpolarized beam. In a preferred embodiment of the present invention, the light beam forms a substantially normal angle of incidence with respect to the plane of the optical plate.

In step 402, a set of background optical measurements are recorded at a set of angular positions of the optical plate. The background optical measurements are performed when no experimental fluid sample is present. In one embodiment, background measurements are conducted with no fluid whatever present in the measurement chamber of the rheometric system, so that the optical data stored from the measurements represents the effects of light interaction with the optical plate alone. In other embodiments, a background measurement fluid is present in the measurement chamber during the background optical measurements. In such a case, the recorded optical data represents effects on an incident light beam of both the rotating optical plate and the background measurement fluid. For example, in step 402, a background (index matched) measurement fluid whose refractive index substantially matches the index of refraction of the experimental fluid sample may be used.

Such a procedure is useful to account for optical plate/fluid interface effects that occur due to mismatch between the refractive index of the optical plate and the actual fluid sample. By emulating the refractive index of the fluid sample in a background measurement, both attenuation of incident light due to the optical plate, and scattering of the light beam at the fluid/optical plate interface can be subtracted or otherwise used to correct for actual experimental fluid sample optical data, which in general reflects the effects of the optical plate, the plate/fluid interface, and the fluid sample optical properties of interest (such as birefringence, dichroism, etc.) on a light beam. Examples of index matching fluids that can be employed in a background measurement in step 402 include the actual solvent to be used in an experimental fluid sample to be subsequently measured, such as a polymer solution; a low molecular weight polymer or oligomer fluid that is related to the polymer fluid to be studied in the experimental fluid sample; a monomer fluid precursor of a polymer fluid to be studied in the experimental fluid sample.

The set of angular plate positions on an optical plate can be chosen in different ways. In one embodiment, equally spaced measurements can be made along an entire circumference of a circle by determining the rotational period of the optical plate (the time required to make one revolution) and taking measurements at equally spaced time intervals where each interval is an integral divisor of the rotational period. In one embodiment of the present invention, the absolute spacing between adjacent positions of the set of angular positions is such that the incident beam does intersect overlapping optical plate regions in adjacent positions. For example, in preferred embodiments of the present invention, the incident beam is fixed to intersect the optical plate at a predetermined radial distance r from the center of the optical plate. When the optical plate rotates, a given angular spacing (□) between adjacent positions corresponds to an absolute spacing D, based on the magnitude of r. For small □D~rsin □. Thus, for example, in the case of a 1 mm diameter laser beam at a radius r, □ can be chosen so that D exceeds 1 mm.

In other words, as the optical plate undergoes rotation, only plate positions (at radius r) corresponding to the designated angular positions are measurable by the laser beam. The size (diameter) of each measurable portion of the optical plate is determined by the diameter of the laser beam. Thus, for example, to avoid overlap, wherein a given portion of the optical plate is measured both at a first angular position and an adjacent angular position, the angular spacing is set such that the center to center distance (D) of the adjacent portions is greater than the beam diameter of the laser beam when it intersects the optical plate. Accordingly, measurable portions of the optical plate are laser-beam-diameter-sized areas of the optical plate that correspond to the designated angular positions to be measured. Portions of the optical plate lying between adjacent measurable portions are not measured. However, in other embodiments ☐ can be chosen such that D is less than the beam diameter, and the incident beam does overlap plate regions in adjacent positions.

In step 404, the set of background optical measurements is mapped to a respective set of plate angular positions, as described in the following discussion. Each given optical measurement recorded in step 402 can be correlated (mapped) to a portion of the optical plate that intercepts the light beam used to produce the given optical measurement, by noting the angular position of a rotating point with respect to a fixed reference point when the optical measurement is made. For example, referring again to FIG. 2a, after optical detector 214 records a series of measurements of transmitted beam 212 taken when optical plate 206 is rotated through the set of positions, the measurement data is forwarded to processor 216 and stored in memory 217. In addition, position transducer 218 records and forwards for storage in memory 217 a set of angular positions of point P with respect to point R (termed "plate angular positions") recorded over the same time span within which the optical measurements are performed. The optical measurement data can then be mapped to the set of angular positions, by arranging a data structure 224c, as illustrated in FIG. 5.

Figure 5:
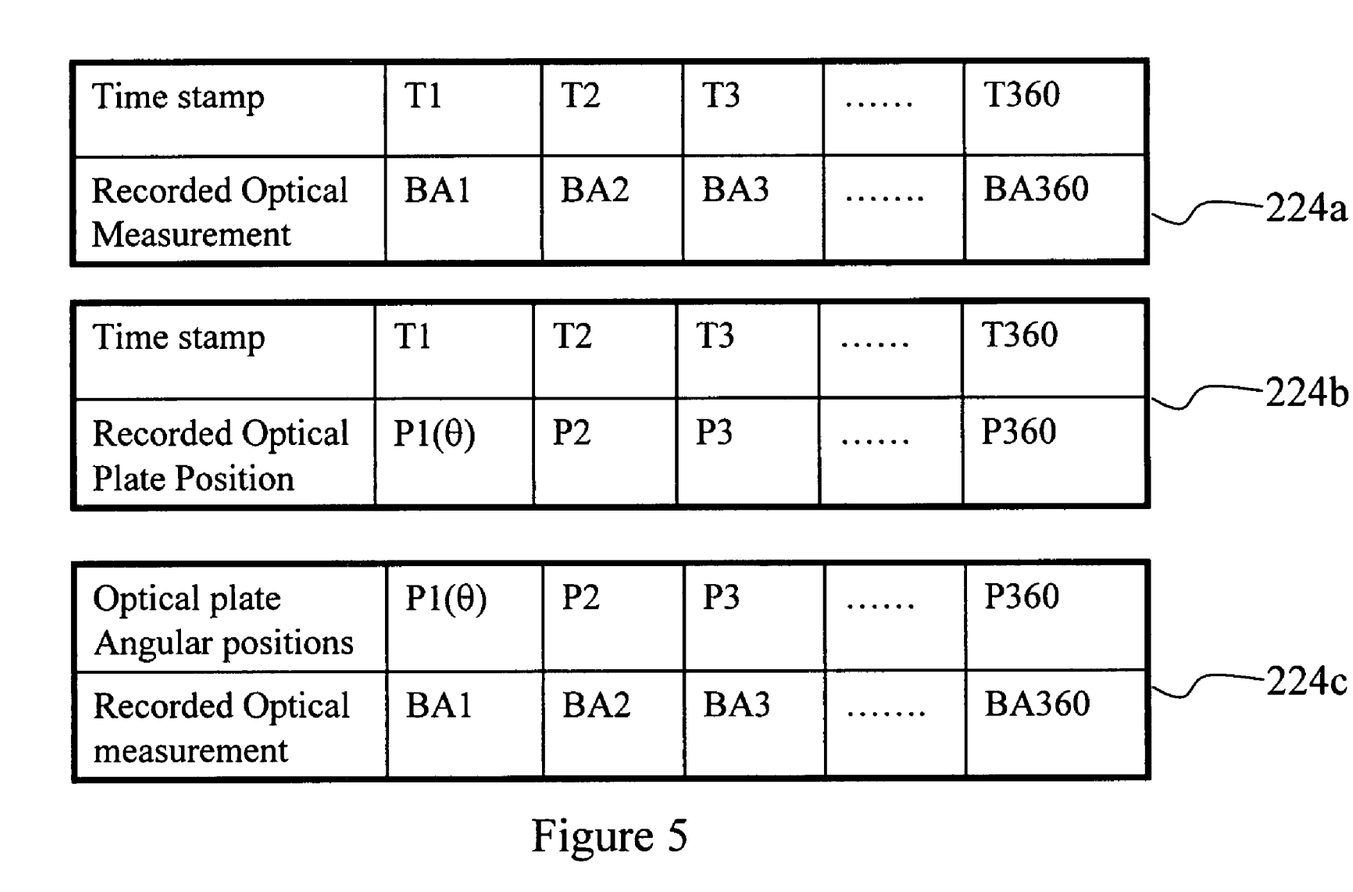
FIG. 5 illustrates an example of mapping of background optical measurement data to an optical plate position, according to one embodiment of the present invention.

FIG. 5 illustrates an example of mapping of optical measurement data to a plate angular position, according to one embodiment of the present invention. For example, referring also to FIG. 2a, while optical plate 214 is rotating, at a set of predetermined time intervals, a common clock (not shown) could be used to trigger position transducer to output the angular position of plate 206 while simultaneously triggering detector 214 to record optical data. Thus, both plate angular position and optical measurements are recorded at substantially the same set of times. Each time of the set of times is represented in a column of data structures 224a-c (shown generally as 224 in FIG. 2a). Times T1-T360 correspond to a time stamp in which respective optical measurements are recorded. The term "time stamp" refers to an absolute time at which a measurement or other event takes place. Optical measurements BA1-BA360 in data structure 224a are, for example, measurements of the intensity of transmitted beam 212. For example, as suggested by the arrangement of data structures 224a-c, which each contain 360 columns, optical measurements can be set to be recorded at a rate of 360 equally spaced measurements per revolution of optical plate 206. Thus, T2-T1=T3-T2, etc. The time interval between optical measurements is accordingly adjusted based on the rotation speed of optical plate 206. Accordingly, during optical measurements taken over one complete rotation of optical plate 206, 360 time stamps are recorded and grouped in data structure 224a with their corresponding optical measurements.

Data structure 224b represents a similar arrangement to that of 224a, where each column represents a time stamp and corresponding plate angular position. Preferably, the set of time stamps in 224a and 224b are substantially the same. Thus, a triggering event that triggers both position transducer 218 to output angular position data and detector 214 to record optical measurement data, can result in substantially the same time stamp for both sets of data. Data structures 224a and 224b can then be combined into data structure 224c as illustrated. Data structure 224c, which represents the mapping of predetermined optical plate angular positions to corresponding optical measurements, thus contains a set of background optical measurements BA (n=1-360) and corresponding optical plate positions that represent the respective angular positions of an optical plate (for example, plate 206) with respect to a reference at the time when the set of optical measurements are recorded.

In the example of FIG. 5, each column of data structure 224c represents a distinct plate angular position of optical plate 206 (P1-P360) with respect to a common reference. For example, referring also to FIG. 2a, P1 may represent an angular position of 1 degree rotation of point P with respect to R, P2 an angular position of 2 degrees with respect to R, etc. Thus, data structure 224c as illustrated in FIG. 5 contains 360 equally spaced plate angular positions. In other embodiments a greater number or a lesser number of plate angular positions can be used for data structure 224.

As mentioned above, the angular spacing between adjacent recorded plate angular positions that is represented in the columns of data structure 224c is determined by a combination of optical plate rotational speed and the time interval between recorded measurements. As is known to those of ordinary skill, modern encoders can resolve angular position in microradian increments. Accordingly, in one embodiment of the present invention, the values Pn (☐) of optical plate positions that are stored in data structure 224c can be recorded with microradian precision. Thus, referring to the example of FIG. 5, if adjacent angular positions at which measurements are to be performed are nominally set to be one degree apart, any actual variation in angular separation between adjacent positions from nominal can be recorded to a high degree of accuracy.

In one embodiment of the invention, optical data is mapped according to plate angular position based on multiple revolutions of an optical plate. For example, the entries of data structure 224c could represent average values taken over a series of optical plate rotations. In embodiments of the present invention where the position transducer is a rotary optical encoder, a fixed reference point can be used to register the passing of a rotating point (see P, R of FIG. 2b) during each revolution, such that the set of plate angular positions is the same during each subsequent revolution. Thus, each column of data structure 224c could represent the average position during a series of complete 360 degree rotations based on a predetermined angular position. In addition, repeated optical measurements recorded at each nominal plate angular position could be stored separately, so that variation (precision) in the optical measurement, as well as an average value can be established.

In step 406 an experimental fluid sample whose properties are to be measured is supplied in a rheometer chamber such that it makes intimate contact with a rotating optical plate.

In step 408 fluid sample optical measurements are recorded at a set of times, and subsequently mapped to those plate angular positions corresponding to the set of times. Thus, referring to FIGS. 2a and 6, "mapped" data structure 226c, derived from data structures 226a and 226b (shown generally as 226 in FIG. 2a), represents a set of fluid sample optical measurements (SA1-SA360) and corresponding plate angular positions (PSA1-PSA360) that are recorded at the same set of respective times (TS1-TS360), in the manner described above for FIG. 5. In a preferred embodiment of the present invention, the set of specified angular plate positions (for example, PSA1-PSA360) is the same as the set of plate angular positions (for example, P1-P360) used for background measurements in step 404.

Figure 7:
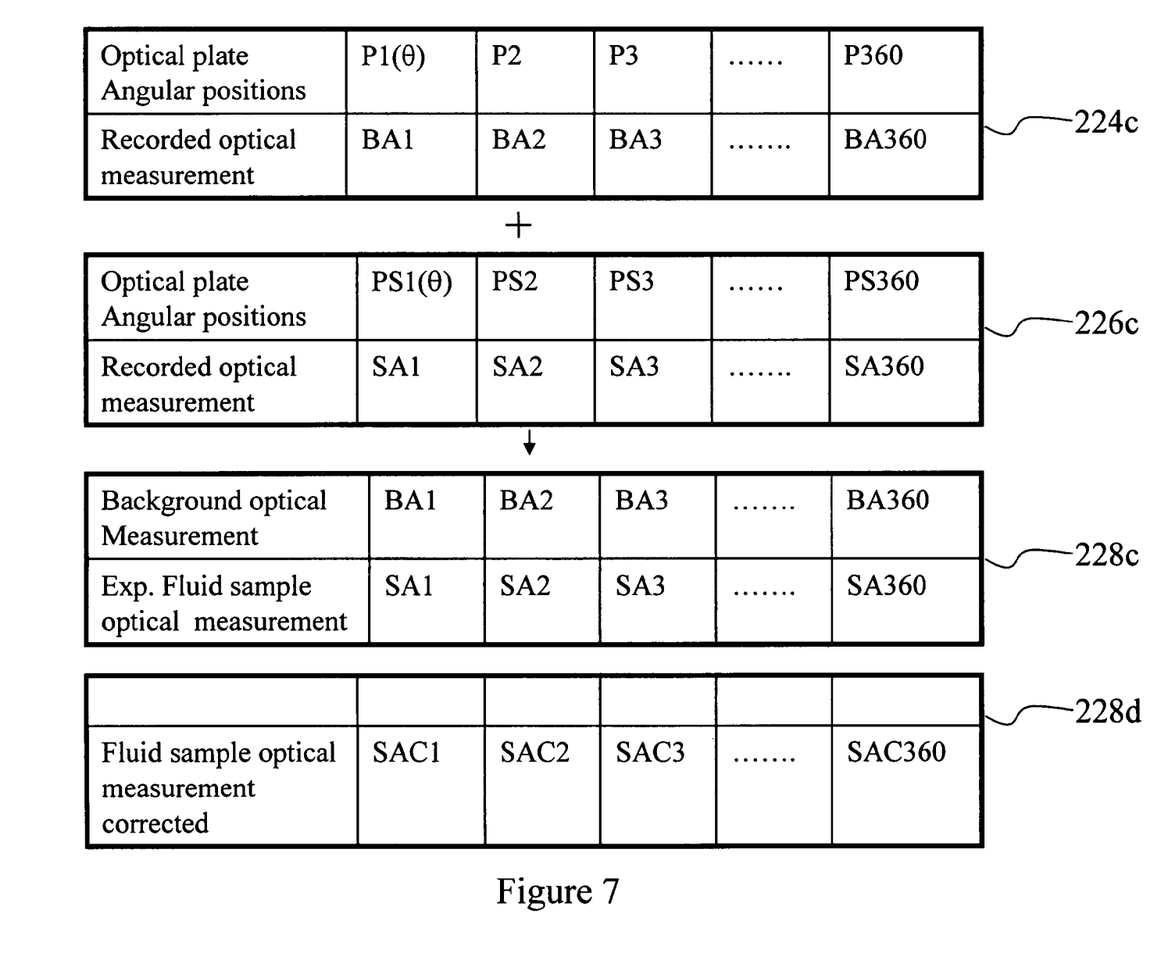
FIG. 7 illustrates mapping of background optical measurement data to experimental fluid sample measurement data according to an embodiment of the present invention.

In step 410, the set of background optical measurements is mapped to the set of fluid sample optical measurements. Referring to FIG. 7, a data structure 228c (shown generally as 228 in FIG. 2a) is created that contains the set of background optical measurements taken at the same set of optical plate angular positions mapped to corresponding fluid sample optical measurements. In one embodiment of the present invention, P1☐=PS1(☐, P2(☐=PS2(☐, etc. In this manner, data structures 224c and 226c can be combined to yield data structure 228c by eliminating the common set of plate angular positions, as shown in FIG. 7.

In step 412, a set of optical data is produced that corresponds to the fluid sample data corrected for the background optical data. In the embodiment of the present invention represented in FIG. 7, there is a one to one correspondence between background optical data (BA) and fluid sample optical data (SA). Accordingly, as illustrated in data structure 228d of FIG. 7, a set of data SACISAC360 is produced that represents fluid sample data collected over a range of plate positions (PS1-PS360) where each fluid sample optical measurement is corrected by the corresponding background optical measurement collected at the same plate position. Thus, variations in plate optical properties as a function of plate position are corrected for in a spatially accurate manner.

Figure 6:
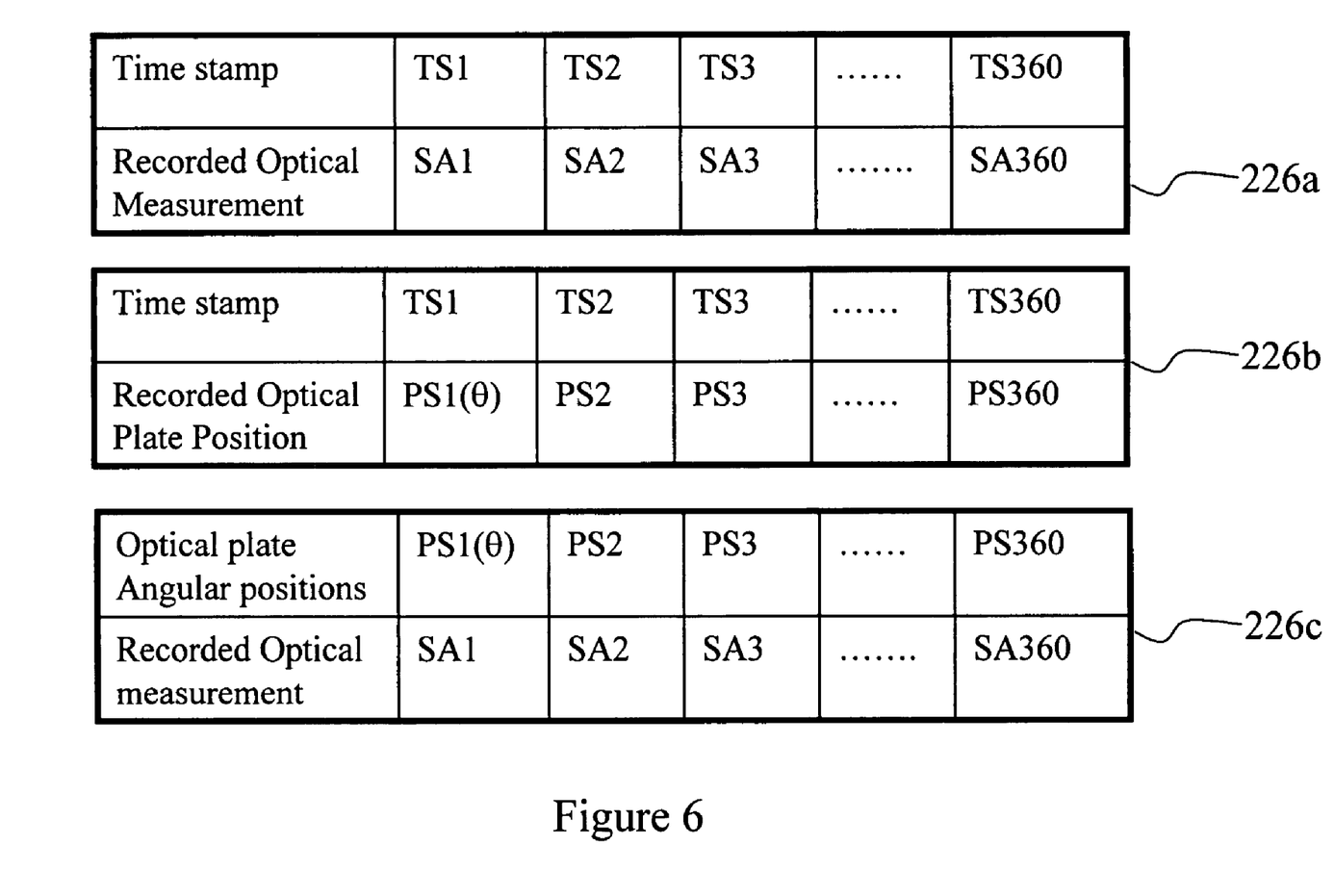
FIG. 6 illustrates an example of mapping of experimental fluid sample optical measurement data to an optical plate position, according to one embodiment of the present invention.

In the data structures illustrated in FIGS. 5-7, the measurement entry for a recorded optical measurement at any given plate position (corresponding to any column within the data structures), for example, P1(☐), may correspond to only a single background measurement or fluid sample measurement. However, in other embodiments, a plurality of measurements can be made and recorded at each plate angular position both during background measurement and during experimental fluid sample measurement. For example, a birefringence measurement conducted at each specified plate angular position could comprise a first measurement performed using a polarizer adjusted to a first position, followed by a second measurement performed using a polarizer adjusted to a second position. This procedure could be conducted for both background and experimental fluid sample measurements, such that background data collected from the first and polarizer positions are subtracted from experimental fluid sample data collected from the respective first and second polarizer positions. Accordingly, two sets of background corrected experimental fluid sample data would be produced, corresponding to a set of optical data collected at a plurality of plate angular positions using a first polarizer orientation, and a set of optical data collected at a plurality of plate angular positions using a second polarizer orientation, as suggested by FIGS. 3a and 3b.

The above procedure facilitates lowering of detection limits and sensitivity for optical properties of fluids to be studied in-situ in a rheometer in conjunction with viscoelastic properties. As mentioned before with reference to FIGS. 3a and 3b, subtle differences in optical properties in an actual fluid sample, such as are encountered in many birefringence measurements, can be extracted from experimental data even when those differences may be smaller than variations in optical properties of the equipment (optical plate) used to conduct the experiments.

Although discussed with respect to transmitted light sample measurements, the method described in FIG. 4 can be adapted in other embodiments of the present invention to provide enhanced measurement of experimental fluid sample light scattering properties. Thus, the variation in plate light scattering properties along an arc of a rotating optical plate can be detected by an appropriately positioned light scattering detector and mapped onto actual light scattering properties of an experimental fluid sample subject to rotation of the optical plate over the same arc, resulting in increased precision of light scattering measurements of the actual fluid sample by subtracting out the position dependent light scattering of the optical plate, in accordance with the procedures outlined in FIGS. 5-7.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. Thus, embodiments in which more sophisticated signal processing schemes are used to map background optical plate data to experimental fluid sample are contemplated. Additionally, the mapping procedures disclosed in FIGS. 4-7 can be used in embodiments of the present invention in which optical plates oscillate back and forth around a rotational axis rather than rotate in one continuous direction.

Moreover, background optical measurements and experimental fluid sample optical measurements need not be conducted using the same set of plate angular positions to fall within the scope of this invention, provided that the background and experimental sets of measurements include overlapping regions on an optical plate (for example, one or more plate angular positions in common) from which background corrected experimental sample data can be obtained. For example, background corrected optical data corresponding to a given set of plate angular positions could be obtained by subtracting corresponding background and experimental sample data, in which any or all of the background and/or experimental sample data at the given set of plate angular positions is calculated data, and not measured data. In other words, background measurements could be performed at a first set of plate angular positions, and experimental fluid sample measurements could be performed at a second set of plate angular positions in which the second set of plate angular positions differ in whole of in part from the first set of plate angular positions. Determination of background corrected fluid sample data would then be performed, for example, by subtracting background data from fluid sample optical data values at a third set of plate angular positions that do not correspond to positions of measured background data and/or measured fluid sample data, as described further below.

If desired, the background data corresponding to the first set of plate angular positions could be used to generate a curve, for example, a continuous curve that performs interpolation between measured data points to provide values of optical properties for plate angular positions that are located at points between the first set of plate angular positions. Alternatively, or in addition to interpolation of background data, a similar process could be used to provide interpolation curves for the experimental fluid data collected at the second set of angular positions.

Referring again to FIG. 3a, for example, the SO and O curves could represent interpolation curves based on measurements performed at a first and second set of plate angular positions, respectively. Thus, mapped background optical data, as well mapped fluid sample optical data would first be produced as discrete sets of data points corresponding to the respective first and second set of plate angular positions. The discrete set of data points could then be used to produce curves that represent respective background optical properties and fluid sample optical properties as a function of optical plate angular position, as suggested by the continuous curves of FIG. 3a. A third set of discrete plate angular positions along curve S could be chosen according to any desired criterion. The third set of positions might correspond to any or all positions of the first and second set of plate angular positions.

For example, the first set of plate angular positions might correspond to fifty points that are used to construct curve O. The second set of plate angular positions might correspond to one hundred points that are used to construct curve SO, in which half of the plate angular positions of the second set correspond to (the fifty) respective plate angular positions of the first set, while the other half correspond to positions half-way in between respective plate angular positions of the first set. Accordingly, absorption values could be extracted from curve O that correspond to points halfway between measured background data points, that is, halfway between adjacent positions of the first set of plate angular positions. Thus, a set of one hundred absorption data points from curve O could be stored in a data structure, in which the data points correspond to the second set of plate angular positions, half of the data points being measured, and half being the result of interpolation. The one hundred data points used to construct curve S would thus comprise subtraction of fifty experimentally measured background data points and fifty interpolated data points from one hundred experimentally measured fluid sample data points.

Moreover, the third set of plate angular positions used to construct curve S need not correspond to the second set of data points, but rather could correspond to any plate angular positions, provided that corresponding measured or interpolated data from curves SO and O is available at the desired third set of positions. Finally, even if the first and second sets of plate angular positions used to produce mapped background and fluid sample optical data are the same, a background corrected set of fluid sample data corresponding to a third set of plate angular positions could be produced therefrom in which the third set of plate angular positions differs from the first and second set. In other words, referring again to FIG. 3a, curves SO and O could represent curves constructed from data taken from the same respective sets of plate angular positions. Subtraction of curve O from curve SO to generate background corrected fluid sample data could be performed at a third set of discrete points along the x-axis (plate angular position) where any or all of the plate angular positions in the third set differ from the experimental measurement positions, that is, the first (and second) set of plate angular positions.

Notably, the scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A system for enhancing optical measurements in a rheometer, comprising:
    a light source to provide light incident on a fluid sample;
    a rotatable optical plate that is substantially transparent to the light source and configured to impart a stress or strain within a fluid disposed within the rheometer;
    a position transducer configured to measure a plate angular position of the rotatable optical plate;
    a detector system for measuring transmitted light signals from light passing through the rotatable optical plate; and
    a memory coupled to the detector system and configured to receive and store background optical data and experimental sample optical data based on the transmitted light signals, the memory further including a data structure that is arranged to provide a set of point by point background corrected optical data, wherein each data point of the background corrected optical data corresponds to a unique location of the rotatable optical plate.

2. The system of claim 1, wherein the rotating optical shaft is mechanically detachable from the rotatable optical plate.

3. The system of claim 1, further comprising a processor that is configured to manipulate the background data and experimental sample data to produce the background corrected optical data.

4. The system of claim 1, wherein the detector system comprises:
    an analyzer configured to polarize portions of the modulated beam transmitted by the fluid sample and to pass an analyzed beam;
    a detector that detects the analyzed beam; and
    a scattered light detector for detecting light originating in the modulated beam and scattered from the fluid sample.

5. The system of claim 1, background optical data corresponds to optical measurements performed on light intersecting the rotatable optical plate without the presence of the fluid sample, and wherein the experimental sample optical data corresponds to measurements performed on light intersecting the rotatable optical plate in the presence of the fluid sample.

6. The system of claim 1, wherein the experimental sample optical data corresponds to measurements performed in the presence of an experimental fluid, and wherein the background optical data comprises data from measurements taken in the presence of an index-matched fluid whose index of refraction substantially matches that of the experimental fluid.

7. The system of claim 1, wherein the position transducer is coupled to a rotating shaft that is configured to rotate in unison with the rotatable optical plate.

8. The system of claim 7, wherein the point by point background corrected optical data comprises data taken from optical measurements performed at a plurality of locations on the rotatable optical plate, the plurality of locations corresponding to a plurality of angular positions located around an entire circumference of a circle concentric with a rotation axis of the rotating shaft.

9. The system of claim 8, wherein the plurality of angular positions are regularly spaced.

10. The system of claim 8, wherein each angular position corresponds to a measurable portion of the rotatable optical plate that is configured to intersect the light source, wherein the plurality of angular positions are mutually spaced such that no overlap occurs among measurable portions.

11. An optical rheometer having optical measurement capabilities, comprising:
    a lead optics module that provides a source of polarized laser light incident on a fluid sample;
    a rotary optical encoder coupled to a rotating shaft and configured to measure an angular position of the shaft;
    a rotatable optical plate mechanically fastenable to the rotating shaft;
    a detector system for measuring transmitted light signals from light passing through the rotatable optical plate;

a memory coupled to the detector system that is configured to receive and store background optical data and experimental sample optical data based on the transmitted light signals; and a plurality of data structures each configured to provide a set of point by point mapping of optical data to respective optical plate positions, wherein at least one data structure comprises background corrected optical data obtained by mapping point by point background data to respective fluid sample data.

12. The system of claim 11, wherein the lead optics module comprises:

a laser that provides the source of polarized light and is configured to provide a beam incident at a substantially normal angle upon the optical plate, wherein at least a portion of the beam is transmitted through the rotatable optical plate;

a polarizer configured to polarize the incident beam and pass a polarized beam;

a photoelastic modulator configured to receive the polarized beam and to pass a modulated beam containing a first component of the polarized beam that is retarded with respect to a second component;

a quarter wave plate; and a fixed optical plate having a portion that substantially transmits the modulated beam.

13. A system for enhancing optical measurements in a rheometer, comprising:

a sample chamber configured to house, alternately, an experimental fluid sample and an index-matched background fluid having a substantially similar refractive index as that of the experimental fluid sample;

a light source configured to direct light toward fluid contained in the sample chamber;

a rotatable optical plate that is substantially transparent to the light source and configured to impart a stress or strain within a fluid disposed within the sample chamber;

a position transducer configured to measure a plate angular position of the rotatable optical plate;

a detector system for measuring transmitted light signals from light received from the light source and passing through the rotatable optical plate, wherein the system is configured to store data from optical measurements performed on the index-matched fluid and experimental fluid sample in respective background and experimental fluid sample data structures, each of the data structures comprising a plurality of optical measurements made at a corresponding plurality of plate angular positions.

14. The system of claim 13, wherein the detector system comprises:

an analyzer configured to polarize portions of the modulated beam transmitted by the fluid sample and to pass an analyzed beam;

a detector configured to detect the analyzed beam; and a scattered light detector for detecting light originating in the modulated beam and scattered from the fluid sample.

15. The system of claim 13, wherein the position transducer is coupled to a rotating shaft that is configured to rotate in unison with the rotatable optical plate.

16. The system of claim 15, wherein the rotating optical shaft is mechanically detachable from the rotatable optical plate.

17. The system of claim 13, further comprising:

a processor operable on a program that is configured to manipulate the background data and experimental fluid sample data structures to produce a background corrected optical data structure; and a memory coupled to the detector system and configured to receive and store in respective data structures the background optical data and the experimental fluid sample optical data, and configured to the background corrected optical data structure.

18. The system of claim 17, wherein the background data structure, experimental fluid sample data structure, and background corrected optical data structure each comprise a set of optical values that are point by point data mapped to corresponding locations on the rotatable optical plate from which the corresponding set of optical values are derived.

19. The system of claim 18 wherein each of the background data structure and the experimental fluid sample data structure comprise a common set of plate angular positions, wherein the background corrected optical data structure comprises a plurality of data points resulting from point by point subtraction of the background optical data from the experimental fluid sample data.

20. The system of claim 18, wherein the corresponding locations comprise a plurality of angular positions located around at least a portion of a circumference of a circle concentric with a rotation axis of the rotating shaft.

21. The system of claim 20, wherein the plurality of angular positions are regularly spaced.

22. The system of claim 20, wherein each angular position corresponds to a measurable portion of the rotatable optical plate that is configured to intersect the light source, wherein the plurality of angular positions are mutually spaced such that no overlap occurs among measurable portions.

* * * * *